US012692226B2

(12) United States Patent
Taulou et al.

(10) Patent No.: US 12,692,226 B2
(45) Date of Patent: Jul. 28, 2026

(54) PROCESS FOR THE CATALYTIC PRODUCTION OF AN ANALOGUE OF METHIONINE

(71) Applicant: ADISSEO FRANCE S.A.S., Antony (FR)

(72) Inventors: Félix Taulou, Lyons (FR); Didier Morvan, Mornant (FR); Virginie Belliere-Baca, Millery (FR); Dorothée Laurenti, Neyron (FR)

(73) Assignees: ADISSEO FRANCE S.A.S., Paris (FR); CENTRE NATIONAL DE LA RECHERCHE SCIENTIFIQUE, Paris (FR); ECOLE CENTRALE DE LILLE, Villeurbanne (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 556 days.

(21) Appl. No.: 18/032,872

(22) PCT Filed: Oct. 20, 2021

(86) PCT No.: PCT/FR2021/051837
§ 371 (c)(1),
(2) Date: Apr. 20, 2023

(87) PCT Pub. No.: WO2022/084632
PCT Pub. Date: Apr. 28, 2022

(65) Prior Publication Data

US 2024/0034716 A1 Feb. 1, 2024

(30) Foreign Application Priority Data

Oct. 23, 2020 (FR) ...................................... 2010876

(51) Int. Cl.
*C07C 319/20* (2006.01)
*B01J 21/04* (2006.01)
(Continued)

(52) U.S. Cl.
CPC ............ *C07C 319/20* (2013.01); *B01J 21/04* (2013.01); *B01J 21/063* (2013.01); *B01J 21/066* (2013.01);
(Continued)

(58) Field of Classification Search
CPC ...... C07C 319/20; C07C 391/00; B01J 35/61; B01J 21/04; B01J 21/063; B01J 21/066; B01J 27/053; B01J 37/20
See application file for complete search history.

(56) References Cited

U.S. PATENT DOCUMENTS

2001/0001105 A1 5/2001 Hsu
2006/0178529 A1 * 8/2006 Weigel et al. ........ C07C 319/12 562/581

FOREIGN PATENT DOCUMENTS

CN 109232342 A 1/2019
CN 109912471 A 6/2019
(Continued)

OTHER PUBLICATIONS

CN109912471A (Zhou et al.; IDS reference; English language machine translation) (Year: 2019).*
(Continued)

*Primary Examiner* — Amy C Bonaparte
*Assistant Examiner* — Derek Rhoades
(74) *Attorney, Agent, or Firm* — Oliff PLC

(57) ABSTRACT

A method for preparing 2-hydroxy-4-methylthiobutyric acid (HMTBA) or 2-hydroxy-4-methylselenobutyric acid (HMSeBA) by catalytic conversion of 2-hydroxy-4-methylthiobutyronitrile or 2-hydroxy-4-methylselenobutyronitrile,
(Continued)

Selectivity and conversion as a function of time with $TiO_2$ respectively, where said conversion is carried out in the presence of water and at least one weak acid and one catalyst comprising at least one of alumina, titanium dioxide and zirconia.

8 Claims, 1 Drawing Sheet

(51) Int. Cl.

| | |
|---|---|
| ***B01J 21/06*** | (2006.01) |
| ***B01J 27/053*** | (2006.01) |
| ***B01J 35/61*** | (2024.01) |
| ***B01J 37/20*** | (2006.01) |
| ***C07C 391/00*** | (2006.01) |

(52) U.S. Cl.

CPC ............ *B01J 27/053* (2013.01); *B01J 35/61* (2024.01); *B01J 37/20* (2013.01); *C07C 391/00* (2013.01)

(56) References Cited

FOREIGN PATENT DOCUMENTS

| | | | |
|---|---|---|---|
| CN | 111116437 | A | 5/2020 |
| FR | 2919607 | A1 | 2/2009 |
| JP | 393754 | A | 4/1991 |
| WO | 2004089863 | A1 | 10/2004 |
| WO | 2008049927 | A1 | 5/2008 |
| WO | 2018167405 | A1 | 9/2018 |

OTHER PUBLICATIONS

Poult. Sci. 2006, 85, 1932-1938 (MartÃ-n-Venegas et al.) (Year: 2006).*

Can. J. Chem. Eng. 2019, 97, 2781-2791 (Bardestani et al.) (Year: 2019).*

International Search Report for corrsponding application PCT/FR2021/051837 filed Oct. 20, 2021; Mail date Jan. 19, 2022.

Saudi Arabic Office Action for corresponding U.S. Appl. No. 18/032,872; Report dated Apr. 23, 2025.

* cited by examiner

[FIG. 1]
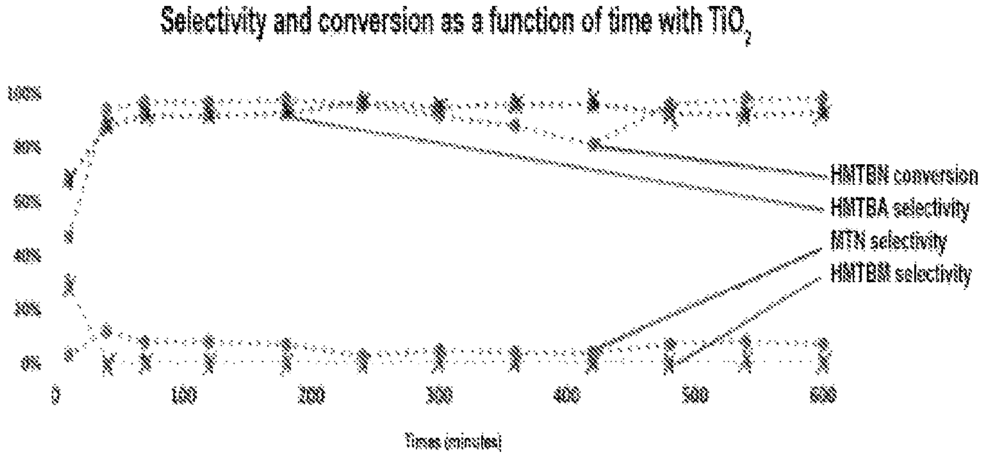
[FIG. 2]
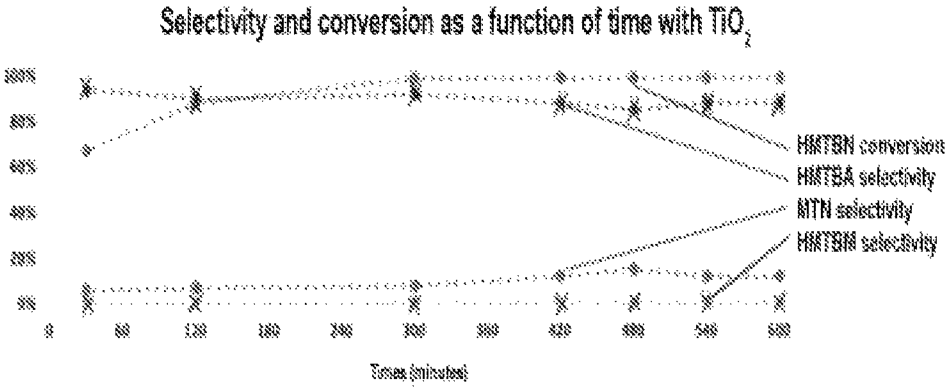

PROCESS FOR THE CATALYTIC PRODUCTION OF AN ANALOGUE OF METHIONINE

TECHNICAL FIELD

The disclosure relates to an improvement of a method for producing 2-hydroxy-4-methylthiobutyric acid, a methionine analogue, or its selenium correspondent, 2-hydroxy-4-methylselenobutyric acid, from 2-hydroxy-4-methylthiobutyronitrile or 2-hydroxy-4-methylselenobutyronitrile, respectively.

BACKGROUND

The 2-hydroxy-4-methylthiobutyric acid (HMTBA), which is the hydroxy analogue of methionine, its salts, its chelates, in particular metal chelates (of Zn, Ca, Mn, Mg, Cu, Na, etc.) and its esters, such as the isopropyl and tert-butyl esters of HMTBA, are widely used in animal nutrition. The selenium derivatives of this acid, of these salts, of these chelates and of these esters are also constituents of major interest in animal nutrition.

The preparation of 2-hydroxy-4-methylthiobutyric acid can be carried out by different methods involving various synthetic intermediates, and in particular 2-hydroxy-4-methylthiobutyronitrile (HMTBN) and 2-hydroxy-4-methylthiobutyramide (HMTBM).

The document US2001/0001105A1 describes a continuous method for the synthesis of 2-hydroxy-4-methylthiobutyric acid (HMTBA) from 2-hydroxy-4-methylthiobutyronitrile (HMTBN) according to which, in a first step, the HMTBN is hydrolyzed into 2-hydroxy-4-methylthiobutyramide (HMTBM) in the presence of an aqueous solution of a mineral acid such as sulfuric acid, then, in a second step, the HMTBM is hydrolyzed into HMTBA. This method has the disadvantage of using large amounts of sulfuric acid, the latter being generally used in excess with respect to the HMTBN, resulting in the formation of large amounts of co-products such as ammonium bisulfate, which must be separated and which, furthermore, are difficult to recycle. This method also requires long residence times in the range of a few hours.

According to document WO2004/089863A1, a method for producing the ammonium salt of HMTBA from the nitrile precursor of HMTBA, HMTBN, according to which HMTBN in aqueous solution, placed in the presence of a titanium-based catalyst, is converted in a single step to the ammonium salt of HMTBA is known. This synthesis also leads to the formation of methionine and HMTBM, and the reported ammonium salt yields of HMTBA are in the range of 1%. They are too insufficient to envisage an application of this method on an industrial scale.

SUMMARY AND DESCRIPTIONS

The present disclosure provides an alternative to the existing methods making it possible both to dispense with the use of sulfuric acid and to combine the hydration and hydrolysis stages in a single catalyzed stage and to lead to yields of HMTBA or in its selenium correspondent, exceptionally and unexpectedly high.

It was discovered according to the disclosure that the hydroxy-nitrile intermediate (HMTBN or its selenium equivalent) could be converted into 2-hydroxy-4-methylthiobutyric acid (or into seleno-hydroxy-methionine) in a single step, in the presence at least one catalyst and a weak acid. The accessibility and performance of this conversion are such that its conversion to industrial production of the hydroxy analogue of methionine is possible. Compared to the known synthetic methods and the developed improvements which could be made thereto but which are insufficiently beneficial for the conventional industrial methods to be modified, the present disclosure represents a real advance. Significant yields are obtained in a very short time and this method avoids the consumption of sulfuric acid and the formation of co-products or synthetic intermediates.

The disclosure provides a method for preparing the hydroxy analogue of methionine or the selenium hydroxy analogue of methionine by catalytic conversion of 2-hydroxy-4-methylthiobutyronitrile or 2-hydroxy-4-methylselenobutyronitrile, respectively, said conversion being carried out in the presence of water and at least one weak acid and one catalyst comprising at least one of alumina, titanium dioxide and zirconia.

According to the disclosure, the hydroxy-nitrile compound is directly converted into hydroxy-acid, after conversion of the ammonium salt of the hydroxy-acid according to conventional techniques, without having to resort to a heavy separation step resulting in a considerable economic gain.

Before exposing the disclosure in more detail, certain terms used in this text are defined.

The term hydroxy acid is used interchangeably with 2-hydroxy-4-methylthiobutyric acid or 2-hydroxy-4-methylselenobutyric acid, considered together or alone. L the term hydroxy-nitrile refers to both 2-hydroxy-4-methylthiobutyronitrile and 2-hydroxy-4-methylselenobutyronitrile, considered together or alone, and the term hydroxy-amide refers to 2-hydroxy-4-methylthiobutyramide or 2-hydroxy-4-methylselenobutyramide, considered together or alone.

By weak acid according to the disclosure is meant any organic or mineral acid whose constant $pK_a$ is at least 1 and at most 10 at 25° C. or any compound or mixture behaving in this way. By way of illustration of a weak organic acid, mention may be made of carboxylic acids and polyacids, which may or may not carry one or more functions, for example selected from OH, C═O, such as acetic acid, formic acid, and by way of illustration of a weak mineral acid, mention may be made of phosphoric acid, dihydrogen phosphate, hydrofluoric acid (HF), hypochlorous acid (HOCl), boric acid ($H_3BO_3$), sulfurous acid ($H_2SO_3$), hydrocyanic acid (HCN).

The term catalyst as used generally refers to the active phase of the catalyst, without excluding the fact that the catalyst may be doped and/or supported.

By alumina, titanium dioxide and zirconia are meant all polymorphs, if any, of aluminum oxide $Al_2O_3$, titanium dioxide $TiO_2$ and zirconium dioxide $ZrO_2$, respectively, these forms being well known for those skilled in the art. The catalyst can also be a two or three-fold combination of alumina, titanium dioxide and zirconia. It can also comprise any other entity promoting its catalytic function.

The characteristics, applications and advantages of the disclosure are exposed below in more detail, it being understood that these characteristics can be considered independently of one another, or in combination, whatever the combination.

The weak acid is preferably an organic acid having one or more carboxylic groups or a mineral acid, having a $pK_a$ of at least 1 at 25° C., and preferably at most 10, more preferably at most 7 at 25° C. In a practical interest, it has a boiling point less than or equal to 170° C. and preferably less than or equal to 150° C., or even less than or equal to 120° C., in order to be more easily separated from the reaction medium, usually by distillation. Such acids which can be used according to the disclosure are in particular selected from formic acid, acetic acid, propionic acid, linear or branched butanoic acid, pentanoic acid, carbonic acid, glycolic acid, thioacetic acid, cyanoacetic acid, lactic acid, pyruvic acid, oxalic acid, methionine or its selenium equivalent, or the hydroxy analogue of methionine or its selenium equivalent. These acids can be used alone or in any mixture with one another. According to one variant, they are selected from formic acid, acetic acid, propionic acid, linear or branched butanoic acid, pentanoic acid, carbonic acid, glycolic acid, thioacetic acid, cyanoacetic acid, lactic acid, pyruvic acid and oxalic acid. Preferably, the used acids are formic acid, acetic acid and/or propionic acid. According to another variant of the disclosure, the weak acid is a mineral acid such as phosphoric acid, dihydrogen phosphate, used alone or as a mixture.

Said weak acid is added in a molar ratio of weak acid to hydroxy-nitrile of 0.001 to 50, or even 0.001 to 30 and even 0.001 to 10 or even 0.001 to 1. In practice, the molar concentration of the weak acid in the reaction medium varies from 0.05 M to 10 M, preferably from 0.1 M to 2 M and even more preferably from 0.2 M to 1 M. According to the disclosure, the catalyst is selected from alumina, titanium dioxide and zirconia; this compound constitutes at least the active phase of the catalyst, optionally the support. Thus, if the catalyst does not consist entirely of one or more of said oxides, it can comprise any other compound which does not affect the performance of the catalyst, or even reinforces it. In a variant of the disclosure, the catalyst consists of one of said oxides.

The catalyst can be doped and/or supported. It can be doped with any element or compound conventionally used and well known to those skilled in the art. By way of illustration, the doping of the catalyst can be carried out by one or more compounds selected from sulphates ($SO_4$), phosphates ($PO_4$), tungstates ($WO_3$), borates ($B_2O_3$), heteropolyacids corresponding to the one of the formulas $H_nXM_{12}O_{40}$ and $H_nX_2M_{18}O_{62}$ in which n is an integer preferably not exceeding 10, X represents Si, Ge, P or As and M represents Mo or W, such as phosphomolybdic acid of formula $H_6P_2Mo_{18}O_{62}$, as well as any other dopant compound providing acidity to the catalyst. The following compounds $PO_4$, $SO_4$ and $H_6P_2Mo_{18}O_{62}$ are to be preferred. If the catalyst does not consist of alumina, titanium dioxide and/or zirconia, it can also be supported by any other compound conventionally used and well known to those skilled in the art, and in particular silica and silicoaluminates.

According to the disclosure, all of the solid catalysts mentioned above can be in powder form or preferably in the form of beads, extrudates, tablets, trilobes or any other form allowing it to be used in a continuous reactor, of the type fixed bed or others or in batch mode in an open or pressurized reactor.

Said catalyst advantageously has a specific surface area of at least 10 $m^2/g$. Below this limit, the performance of the catalyst drops rapidly, notably with a decline in the selectivity for hydroxy-acid in favor of that for hydroxy-amide and a decrease in the conversion of hydroxy-nitrile. This observation is applied to the selenium equivalent. Advantageously, the specific surface is at least 50 $m^2/g$. The upper limit of the specific surface is not critical in the context of the disclosure, the latter being imposed by the active phases commercially available. The specific surface area values indicated in this text are determined by the most common method, namely nitrogen physisorption and calculated by the BET method.

In a preferred implementation of the method of the disclosure, the catalyst is present in a concentration by mass of 0.1% to 200% relative to the mass of HMTBN, preferably from 0.5% to 100% and better still from 1% to 50%.

According to the disclosure, different equipment can be envisaged for carrying out the reaction in batch or continuously: the solid catalyst, doped or not, can be immobilized in a reactor in the form of grains or extrudates or any other form or supported on a metal foam. The reactor associated with this type of catalyst is preferably a tubular or multitubular fixed bed, operating in trickle or flooded isothermal or adiabatic mode, or an exchange reactor coated with catalyst.

The conversion of HMTBN within the scope of the disclosure is advantageously carried out at a temperature ranging from 20° C. to 200° C., preferably from 50° C. to 180° C., and better still from 80° C. to 170° C. It has been observed, over a reaction period ranging from about 10 minutes to 3 hours, that at a temperature below 20° C., the reaction is greatly slowed down, and that from 180° C., more as the temperature increases, the more the selectivity for methionine and dinitrile and methionine polypeptide increases to the detriment of that for 2-hydroxy-4-methylthiobutyric acid. The selectivity to hydroxy acid is highest in the range 100° C. to 180° C.

In the context of the disclosure, the contact times between the reaction mixture containing water, the hydroxy-nitrile and the acid with the catalyst range from 30 seconds to 1 hour, preferably from 1 minute to 30 minutes and even more preferably from 2 minutes to 20 minutes.

Hydroxy-nitrile is generally in aqueous solution. This may have been prepared for the implementation of the method. The weak acid used in the reaction can be added to the aqueous hydroxy-nitrile solution or added via a mixer before entering the catalytic reactor.

The concentration of hydroxy-nitrile can have an influence on the performance of the method, especially when it is too high. Thus, according to a variant of the disclosure, the hydroxy-nitrile is in aqueous solution in a concentration ranging from 0.01 M to 10 M, preferably from 0.05 M to 1 M. It has been noted that beyond 1 M, if the conversion to hydroxy-nitrile remains strong, the selectivity for hydroxy-acid decreases while those for hydroxy-amide, dinitrile and even polypeptide, respectively, increase.

The disclosure also concerns the implementation of the method of the disclosure continuously. According to this variant, the method is carried out under a pressure which may range from 1 to 20 bar, preferably from 2 to 10 bar. Thus, the disclosure provides a device comprising a tank for the hydroxy-nitrile solution and in which a weak acid is added. The resulting hydroxy acid solution is pumped to a reactor which comprises the catalyst and which is heated by means of a sleeve or an oven at a temperature of 80 to 180° C. The reaction medium is withdrawn to a gas/liquid separator from which the gases will be removed and from which the liquid is treated to recover the hydroxy acid. The solution is then evaporated to separate the excess used water and the weak acid which may or may not form an azeotrope, these compounds then being advantageously recycled in the method. Then, the phase containing the hydroxy acid can be stripped to remove all or part of the ammonia that makes up the ammonium salt of the hydroxy acid. Additional electrodialysis steps or other technologies known to those skilled in the art can be envisaged to fully recover the hydroxy acid in its acid form (2-hydroxy-4-methylthiobutyric acid or the corresponding selenium acid) and completely recycling the ammonia formed during the hydrolysis of the HMBTM intermediate in the catalytic step. Advantageously, the recovered ammonia will be recycled upstream of the hydroxy-acid producing method, as in the synthesis of HCN.

BRIEF DESCRIPTION OF THE DRAWINGS

The disclosure and its advantages over the prior art are illustrated in the examples below, in support of the following figures:

FIG. 1 shows the conversion of HMTBN, the selectivity to HMTBA, the selectivity to methionine and the selectivity to HMTBM, as a function of time, of a reaction according to a method of the disclosure under the conditions described in Example 1.

FIG. 2 shows the conversion of HMTBN, the selectivity to HMTBA, the selectivity to methionine and the selectivity to HMTBM, as a function of time, of a reaction according to a method of the disclosure under the conditions described in Example 2.

EXAMPLES

In the experimental part which follows:

Examples 1-6 illustrate various variations of a method of the disclosure;

Examples 7 and 8 illustrate a technique for doping a catalyst to obtain a doped catalyst which can be used in a method of the disclosure, according to a variant such as that which is the subject of Example 6;

Example 9 illustrates a step of separating the hydroxy acid salt into the hydroxy acid; and Examples 10 to 15 illustrate methods outside the disclosure, by way of comparison.

Example 1: Preparation of HMTBA in the Presence of Titanium Dioxide and Acetic Acid, According to the Disclosure The hydrolysis reaction of HMTBN and the conditions under which it is carried out are described in the diagram below.

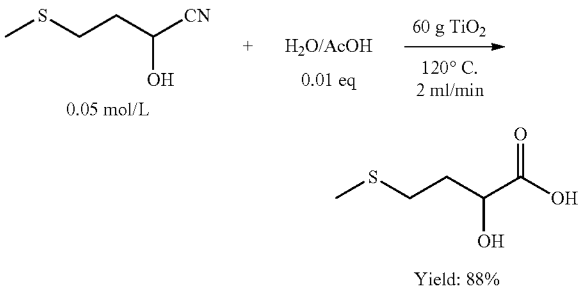

In a 1 liter screw cap bottle, 14.0 g of HMTBN with 2000 ml of $H_2O$ and 60 mg of acetic acid are introduced. The solution is stirred at room temperature with a flow of nitrogen and injected into a tubular reactor heated to 120° C. with a flow rate of 0.05 ml/min (contact time 24 minutes) and containing 60 grams of $TiO_2$ (anatase, 150 $m^2$/g, Norpro, ST 61120).

The reaction is followed by HPLC. The yield of HMTBA is 88%.

Example 2: Preparation of HMTBA in the Presence of Titanium Dioxide and Acetic Acid, According to the Disclosure The hydrolysis reaction of HMTBN and the conditions under which it is carried out are described in the diagram below.

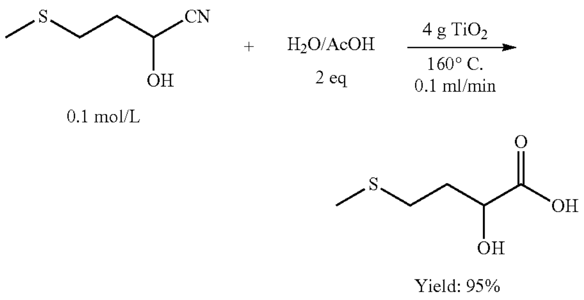

In a 1 liter screw cap bottle, 13.1 g of HMTBN with 990 ml of $H_2O$ and 10 ml of acetic acid are introduced. The solution is stirred at room temperature with a flow of nitrogen, the solution is injected into a tubular reactor heated to 160° C. with a flow rate of 0.1 ml/min (contact time 10 minutes) and containing 4 grams of $TiO_2$ (anatase, 150 $m^2$/g, Norpro, ST 61120). The HMTBA salt obtained is converted into HMTBA by stripping ammonia according to a technique illustrated in Example 9.

The reaction is followed by HPLC: the conversion of HMTBN, the selectivity to HMTBA, the selectivity to methionine and the selectivity to HMTBM, as a function of time are represented in [FIG. 1].

The yield of HMTBA is 95% and 5% of methionine.

Example 3: Preparation of HMTBA in the Presence of Titanium Dioxide and Acetic Acid, According to the Disclosure The hydrolysis reaction of HMTBN and the conditions under which it is carried out are described in the diagram below.

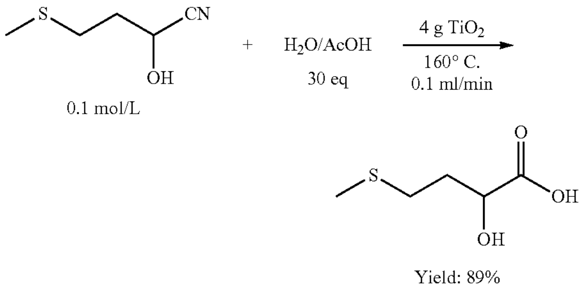

In a 1 liter screw cap bottle, 13.1 g of HMTBN with 800 ml of $H_2O$ and 200 ml of acetic acid were introduced. The solution is stirred at room temperature with a flow of nitrogen, the solution is injected into a tubular reactor heated to 160° C. with a flow rate of 0.1 ml/min (contact time 10 minutes). The reactor contains 4 grams of $TiO_2$ (anatase, 150 $m^2$/g, Norpro, ST 61120). The HMTBA salt obtained is converted into HMTBA by stripping ammonia according to a technique illustrated in Example 9.

The reaction is followed by HPLC: the conversion of HMTBN, the selectivity to HMTBA, the selectivity to methionine and the selectivity to HMTBM, as a function of time are represented in [FIG. 2].

The yield of HMTBA is 89% and 11% of methionine.

Example 4: Preparation of HMTBA in the Presence of Titanium Dioxide and Formic Acid, According to the Disclosure The hydrolysis reaction of HMTBN and the conditions under which it is carried out are described in the diagram below.

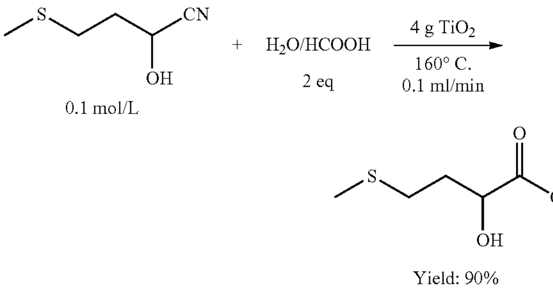

In a 1 liter screw cap bottle, 13.1 g of HMTBN with 990 ml of $H_2O$ and 10 ml of formic acid were introduced. The solution is stirred at room temperature with a flow of nitrogen, the solution is injected into a tubular reactor heated to 160° C. with a flow rate of 0.1 ml/min (contact time 10 minutes). The reactor contains 4 grams of $TiO_2$ (anatase, 150 $m^2/g$, Norpro, ST 61120).

The reaction is followed after 2 hours by HPLC.

The obtained HMTBA salt is converted into HMTBA by stripping ammonia according to a technique illustrated in Example 9.

The yield of HMTBA is 90% and 10% of methionine.

Example 5: Preparation of HMTBA in the Presence of an Alumina Doped with Sulfate and Acetic Acid, According to the Disclosure The hydrolysis reaction of HMTBN and the conditions under which it is carried out are described in the diagram below.

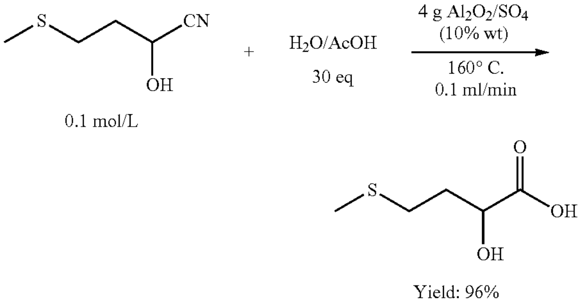

In a 1 liter screw cap bottle, 13.1 g of HMTBN with 800 ml of $H_2O$ and 200 ml of acetic acid were introduced. The solution is stirred at room temperature with a flow of nitrogen, the solution is injected into a tubular reactor heated to 160° C. with a flow rate of 0.1 ml/min (contact time 10 minutes). The reactor contains 4 grams of $Al_2O_3$ (gamma, 300 $m^2/g$, IFPEN, 33006 GFSA 401, alumina doped with 10% by weight of sulfate function).

The reaction is followed after 2 hours by HPLC.

The obtained HMTBA salt is converted into HMTBA by stripping ammonia according to a technique illustrated in Example 9.

The yield of HMTBA is 96% and 4% of methionine.

Example 6: Preparation of HMTBA in the Presence of Zirconia and Acetic Acid, According to the Disclosure The hydrolysis reaction of HMTBN and the conditions under which it is carried out are described in the diagram below.

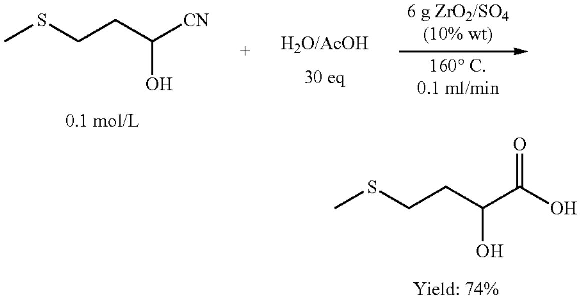

In a 1 liter screw cap bottle, 13.1 g of HMTBN with 800 ml of $H_2O$ and 200 ml of acetic acid were introduced. The solution is stirred at room temperature with a flow of nitrogen, the solution is injected into a tubular reactor heated to 160° C. with a flow rate of 0.1 ml/min (contact time 10 minutes). The reactor contains 6 grams of $ZrO_2$ (monoclinic, 100 $m^2/g$, Norpro, XZ 16075).

The reaction is followed after 2 hours by HPLC.

The obtained HMTBA salt is converted into HMTBA by stripping ammonia according to a technique illustrated in Example 9.

The yield of HMTBA is 74% and 16% of methionine.

Example 7: Preparation of $TiO_2$ Doped with 10% by Weight of Sulfate ($SO_4$) with Sulfuric Acid In a 1 liter flask, 20 g of $TiO_2$ (anatase, 150 $m^2/g$, Norpro, ST 61120) powder with 500 mL of water and 2.04 g of sulfuric acid are introduced. The solution is stirred for 2 hours at room temperature, then the water is evaporated. The obtained powder is then dried at 200° C. for 3 hours and then it is calcined at 700° C. in air for 2 hours. An elemental analysis was carried out to measure the sulfur, an amount of sulfur of 3.4% by mass of catalyst is observed, which corresponds to an amount of sulfate of 10% by mass.

Example 8: Preparation of $TiO_2$ Doped with 10% by Weight of Sulfate ($SO_4$) with Ammonium Sulfate In a 1 liter flask, 20 g of powder $TiO_2$ (anatase, 150 $m^2/g$, Norpro, ST 61120) with 500 ml of water and 2.78 g of ammonium sulphate are introduced. The solution is stirred for 2 hours at room temperature, then the water is evaporated. The obtained powder is then dried at 200° C. for 3 hours and then it is calcined at 700° C. in air for 2 hours. An elemental analysis was carried out to measure the sulfur, an amount of sulfur of 3.2% by mass of catalyst is observed, which corresponds to an amount of sulfate of 9.8% by mass.

Example 9: Conversion of the Ammonium Salt of HMTBA to HMTBA

The HMTBA ammonium salt solution obtained according to the disclosure is concentrated in organics to an organics content of 87% by weight. The temperature of the medium changes from 100 to 130° C. (atmospheric pressure). After this concentration step, the conversion to HMTBA amounts is 21% (mol). Then, a steam stripping phase is carried out. The stripping water is introduced in liquid form. The organic content is kept constant at 87% by weight. The temperature is stationary between 115 and 121° C. The stripping rate is between 3.8 and 4.3 ml/min. After 200 minutes under these conditions, a conversion to HMTBA of 47% is obtained. A further stripping step is carried out to result in HMTBA in yields of around 100%.

Example 10: Preparation of HMTBA in the Presence of Acetic Acid, not Forming Part of the Disclosure The hydrolysis reaction of HMTBN and the conditions under which it is carried out are described in the diagram below.

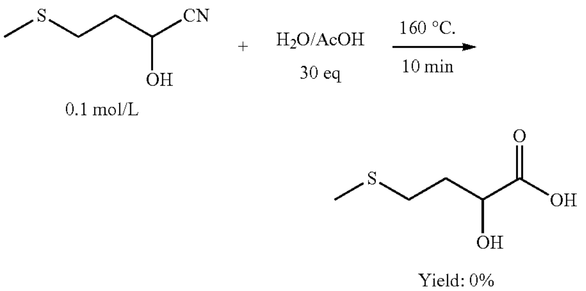

In a 20 ml screw cap bottle, 0.131 g of HMTBN with 8 ml of $H_2O$ and 2 ml of acetic acid were introduced. The solution is stirred at 160° C. for ten minutes.

The solution is analyzed by HPLC, no reaction is observed.

Example 11: Preparation of HMTBA in the Presence of Formic Acid, not Forming Part of the Disclosure The hydrolysis reaction of HMTBN and the conditions under which it is carried out are described in the diagram below.

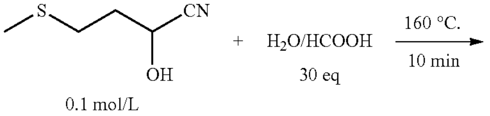

-continued

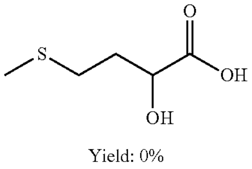

In a 20 ml screw cap bottle, 0.131 g of HMTBN with 9 ml of $H_2O$ and 1 ml of acetic acid were introduced. The solution is stirred at 160° C. for ten minutes. The solution is analyzed by HPLC, no reaction is observed.

Example 12: Preparation of HMTBA in the Presence of Titanium Dioxide, According to the Prior Art The hydrolysis reaction of HMTBN and the conditions under which it is carried out are described in the diagram below.

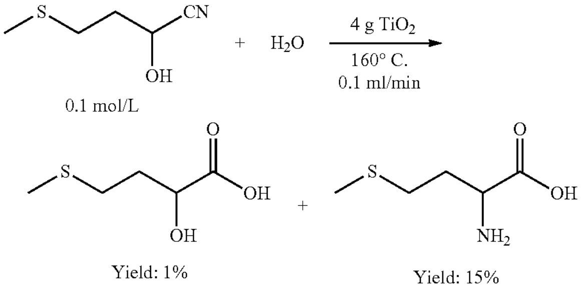

In a 1 liter screw cap bottle, 13.1 g of HMTBN with 1000 ml of $H_2O$ were introduced. The solution is stirred at room temperature with a flow of nitrogen, the solution is injected into a tubular reactor heated to 160° C. with a flow rate of 0.1 ml/min (contact time 10 minutes) and containing 4 grams of $TiO_2$ (anatase, 150 $m^2$/g, Norpro, ST 61120).

The reaction is followed by HPLC, the yield of HMTBA is 1% and 15% of methionine.

Example 13: Preparation of HMTBA in the Presence of a Gamma Phase Alumina, According to the Prior Art The hydrolysis reaction of HMTBN and the conditions under which it is carried out are described in the diagram below.

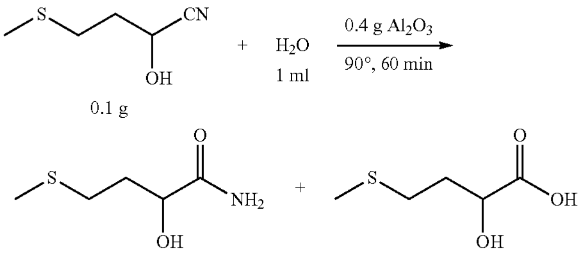

In a 10 ml screw cap bottle, 0.4 g of γ-$Al_2O_3$ (300 $m^2$/g), then 0.1 g of HMTBN (97%) with 1 ml of water were introduced. The solution was heated at 90° C. for 60 minutes after which the solution was filtered and analyzed by proton NMR.

No conversion of HMTBN is observed

Example 14: Preparation of HMTBA in the Presence of a Gamma Phase Alumina, According to the Prior Art The hydrolysis reaction of HMTBN and the conditions under which it is carried out are described in the diagram below.

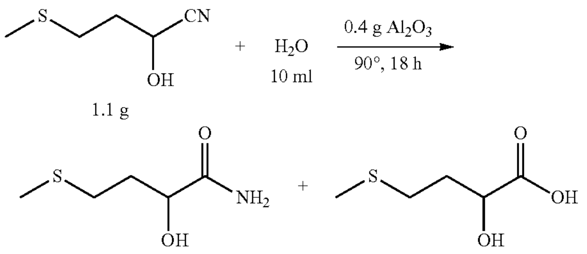

In a 20 ml screw cap bottle, 0.4 g of γ-$Al_2O_3$ (300 $m^2$/g), then 1.1 g of HMTBN (97%) with 10 ml of water were introduced. The solution was heated at 90° C. for 18 hours after which the solution was filtered and analyzed by proton NMR.

A yield of HMTBM of 30% and of HMTBA of 6% is observed.

Example 15: Preparation of HMTBA in the Presence of $TiO_2$ Anatase, According to the Prior Art The hydrolysis reaction of HMTBN and the conditions under which it is carried out are described in the diagram below.

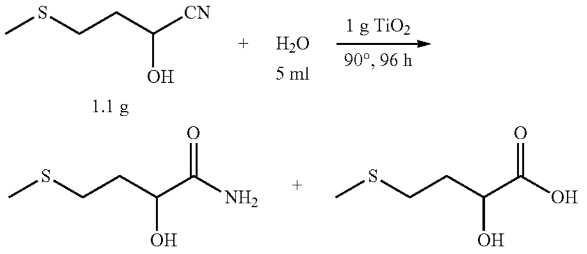

In a 10 ml screw cap bottle, 1 g of $TiO_2$ (as anatase) (90 $m^2$/g), then 1.1 g of HMTBN (97%) with 1 ml of water were introduced. The solution was heated at 90° C. for 96 hours after which the solution was filtered and analyzed by proton NMR No traces of HMTBM or HMTBA are observed. .

The comparison of the results of Examples 1 to 6 according to the disclosure, with those obtained in a method carried out without a catalyst (Examples 10 and 11) or without weak acid (Examples 12 to 15) demonstrates a considerable gain in the performance of the production of a hydroxy acid in a method of the disclosure, which is moreover unexpected.

The invention claimed is:

1. A method for preparing 2-hydroxy-4-methylthiobutyric acid (HMTBA) or 2-hydroxy-4-methylselenobutyric acid (HMSeBA) comprising catalytically converting of 2-hydroxy-4-methylthiobutyronitrile (HMTBN) or 2-hydroxy-4-methylselenobutyronitrile, respectively, wherein said catalytically converting is carried out in the presence of water and at least one weak acid and one catalyst comprising at least one of alumina, titanium dioxide and zirconia, wherein said weak acid is selected from formic acid, acetic acid, propionic acid, linear or branched butanoic acid, pentanoic acid, carbonic acid, glycolic acid, thioacetic acid, cyanoacetic acid, lactic acid, pyruvic acid and oxalic acid-, wherein said catalytically converting consist of converting hydroxy-4-methylthiobutyronitrile or 2-hydroxy-4-methylselenobutyronitrile into 2-hydroxy-4-methylthiobutyric acid or 2-hydroxy-4-methylselenobutyric acid, respectively, and wherein said conversion is carried out in a single step.

2. The method according to claim 1, wherein the molar ratio of the weak acid to 2-hydroxy-4-methylthiobutyronitrile or 2-hydroxy-4-methylselenobutyronitrile, ranges from 0.001 to 50.

3. The method according to claim 1, wherein the catalyst is present in a mass concentration of 0.1% to 200% relative to the mass of HMTBN.

4. The method according to claim 1, wherein 2-hydroxy-4-methylthiobutyronitrile or 2-hydroxy-4-methylselenobutyronitrile is present in an aqueous solution with a concentration ranging from 0.01 M to 10 M.

5. The method according to claim 1, wherein said catalyst has a BET specific surface area of at least 10 $m^2$/g.

6. The method according to claim 1, wherein said catalyst is doped, with one or more compounds selected from sulfates, phosphates, borates, tungstates, heteropolyacids corresponding to one of the formulas $H_nXM_{12}O_{40}$ and $H_nX_2M_{18}O_{62}$ in which n is an integer not exceeding 10, X represents Si, Ge, P or As, and M represents Mo or W, and as well as any other doping compound providing acidity to the catalyst.

7. The method according to claim 1, wherein the conversion is carried out at a temperature ranging from 20° C. to 200° C.

8. The method according to claim 1, wherein it is carried out continuously.

* * * * *